(12) United States Patent
Babcock et al.

(10) Patent No.: US 11,938,250 B2
(45) Date of Patent: Mar. 26, 2024

(54) ARTICLE COATINGS INCLUDING OLIGOMERIZED POLYPHENOL LAYER AND BIOLOGICAL METHODS OF USE

(71) Applicant: Surmodics, Inc., Eden Praire, MN (US)

(72) Inventors: David E. Babcock, Brooklyn Park, MN (US); Sean Lundquist, Chaska, MN (US); Gary Opperman, St. Louis Park, MN (US); Adriyn Torguson, Maple Grove, MN (US); Tim Jentz, Minnetonka, MN (US)

(73) Assignee: Surmodics, Inc., Eden Prairie, MN (US)

( * ) Notice: Subject to any disclaimer, the term of this patent is extended or adjusted under 35 U.S.C. 154(b) by 651 days.

(21) Appl. No.: 16/272,808

(22) Filed: Feb. 11, 2019

(65) Prior Publication Data
US 2019/0275209 A1    Sep. 12, 2019

Related U.S. Application Data

(63) Continuation of application No. 15/502,345, filed as application No. PCT/US2015/044002 on Aug. 6, 2015, now Pat. No. 10,201,637.

(60) Provisional application No. 62/035,173, filed on Aug. 8, 2014.

(51) Int. Cl.
| | | |
|---|---|---|
| A61L 29/08 | (2006.01) | |
| A61K 31/7024 | (2006.01) | |
| A61L 15/44 | (2006.01) | |
| A61L 27/34 | (2006.01) | |
| A61L 27/54 | (2006.01) | |
| A61L 29/06 | (2006.01) | |
| A61L 29/16 | (2006.01) | |
| A61L 31/10 | (2006.01) | |
| A61L 31/16 | (2006.01) | |
| G01N 33/543 | (2006.01) | |

(52) U.S. Cl.
CPC ........ *A61L 29/085* (2013.01); *A61K 31/7024* (2013.01); *A61L 15/44* (2013.01); *A61L 27/34* (2013.01); *A61L 27/54* (2013.01); *A61L 29/06* (2013.01); *A61L 29/16* (2013.01); *A61L 31/10* (2013.01); *A61L 31/16* (2013.01); *G01N 33/54393* (2013.01); *A61L 2300/216* (2013.01); *A61L 2300/418* (2013.01); *A61L 2300/42* (2013.01); *A61L 2400/04* (2013.01); *A61L 2400/18* (2013.01); *A61L 2420/02* (2013.01); *A61L 2420/08* (2013.01)

(58) Field of Classification Search
CPC .................................... A61P 7/04; A61L 5/44
See application file for complete search history.

(56) References Cited

U.S. PATENT DOCUMENTS

| | | | |
|---|---|---|---|
| 5,135,516 A | 8/1992 | Sahatjian et al. | |
| 2006/0210816 A1 | 9/2006 | Finley | |
| 2007/0282422 A1 | 12/2007 | Biggs et al. | |
| 2010/0209472 A1* | 8/2010 | Wang .................... | A61M 25/10 424/423 |
| 2013/0136713 A1 | 5/2013 | Terada et al. | |

FOREIGN PATENT DOCUMENTS

| | | |
|---|---|---|
| JP | 2008237621 | 10/2008 |
| WO | 2007/133479 A2 | 11/2007 |
| WO | 2011/119159 A1 | 9/2011 |
| WO | 2012/158944 A1 | 11/2012 |
| WO | 2014107670 A1 | 7/2014 |

OTHER PUBLICATIONS

Oliveira et al., Natural Products, 2013, 1753-1801).*
Sugiyama et al., J Agric Food Chem. 2007, 55, 4604-4609.*
FoodB:Proanthocyanidin, 1 page.*
Ejima et al. (2013) "On-Step Assembly of Coordination Complexes for Versatile Film and Particle Engineering", Science, 341:154-156.
Ejima et al. (2013) "On-Step Assembly of Coordination Complexes for Versatile Film and Particle Engineering", Science, 341, 28 pages.
Zhang et al. (2009) Grain Dictionary, China Material Press, p. 78, paragraph 3 (machine translation).
Yang et al. (2003) "Tea Polypheno Chemistry", Shanghai Science and Technology Press, p. 32, section 1.3.3 (machine translation).

* cited by examiner

*Primary Examiner* — Kyle A Purdy
(74) *Attorney, Agent, or Firm* — Kagan Binder, PLLC

(57) ABSTRACT

Embodiments of the disclosure include coatings comprising an oligomerized polyphenol layer. The oligomerized polyphenol layer can be used as an intermediate coated layer on a medical device that hydrogen bonds to a synthetic or natural polymer, which in turn can be used as a top coat or further associated with another coated layer. The multilayered coatings can provide properties such as hemocompatibility or lubricity. In other embodiments, the oligomerized polyphenol layer is used on a medical device as a hemostatic layer configured to contact blood and promote coagulation. The oligomerized polyphenol layer can also be used on the inner surface (e.g., inner diameter) of a medical device to prevent bacterial adherence. The oligomerized polyphenol layer can also be used on the surface of a in vitro diagnostic article, or a cell culture device to, promote adsorption of a biological molecule.

17 Claims, 7 Drawing Sheets

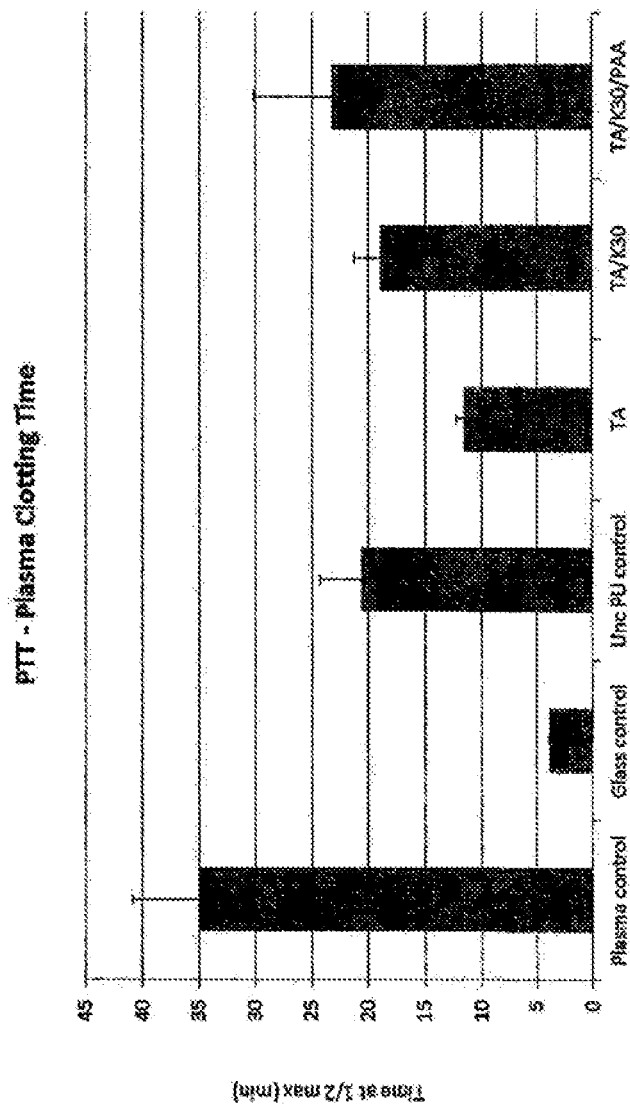

ARTICLE COATINGS INCLUDING OLIGOMERIZED POLYPHENOL LAYER AND BIOLOGICAL METHODS OF USE

PRIORITY

The present Application is a continuation of U.S. patent application Ser. No. 15/502,345, filed Feb. 7, 2017, which claims the benefit from International Application No. PCT/US2015/044002, filed Aug. 6, 2015, which in turn claims the benefit of commonly owned U.S. provisional Application having Ser. No. 62/035,173, filed on Aug. 8, 2014, entitled ARTICLE COATINGS INCLUDING OLIGOMERIZED POLYPHENOL LAYER AND BIOLOGICAL METHODS OF USE, which Applications are incorporated herein by reference in their entireties.

FIELD

The present disclosure relates to coatings for medical, diagnostic, and cell culture articles.

SUMMARY OF THE INVENTION

Embodiments of the disclosure include coatings for various articles, such as medical, diagnostic, and cell culture articles. Embodiments of the disclosure also include methods using the coated articles.

Generally, the articles have a costing that includes a coated layer (e.g., a first coated layer) of oligomerized polyphenol. In some embodiments the articles have at least one different coated layer(s) (e.g., second) including a natural or synthetic polymer that hydrogen bonds with the oligomerized polyphenol. The coatings display desirable properties, and the coating materials and techniques can be used to provide well-formed coatings on various surfaces. The coated articles can be used in various methods, such as methods associated with the implantation of medical devices, the treatment of conditions using an implanted medical device, hemostatic methods including blood clotting and wound healing, in vitro diagnostic methods such as ELISAs, and cell culture methods.

The oligomerized polyphenol can comprise a polyphenol derived from esterification of a composition comprising gallic acid. The oligomerized polyphenol can include, for example, oligomerized tannic acid.

In one embodiment, the disclosure provides a medical device comprising a coating, the coating comprising a first coated layer comprising oligomerized polyphenol, and a second coated layer comprising a synthetic or natural polymer. In the coating the synthetic or natural polymer is hydrogen bonded to the oligomerized polyphenol and the first coated layer is positioned between an article surface and the second coated layer.

The coating can be formed in a method comprising step of applying a first coating composition comprising a polyphenol to a medical device. A first layer comprising oligomerized polyphenol is formed upon application. Next, a second coating composition comprising a synthetic or natural polymer is applied onto the first layer. The synthetic or natural polymer becomes hydrogen bonded to the oligomerized polyphenol.

Medical devices having a first coated layer comprising oligomerized polyphenol include catheters and intravascular prosthesis. In particular, the polyphenol materials a, useful for coating inner surfaces of medical devices, such as the inner diameters of catheters.

Given its ability to provide coatings in a straightforward manner, the disclosure also provides a medical device comprising an inner surface comprising a coating, the coating comprising oligomerized polyphenol. Additional coated layers (e.g., second coated layer) on the oligomerized polyphenol are optional. In one embodiment, the oligomerized polyphenol coating is formed on the inner diameter of a catheter. The inner surface coating can be useful in a method for reducing or preventing the adherence of bacteria on a medical device surface, comprising implanting the device of claim in a patient.

In another aspect of the disclosure, experimental studies revealed that an oligomerized polyphenol coating was surprisingly beneficial for promoting the adsorption of fibrinogen, and for promoting blood clotting. Accordingly, the disclosure also provides a medical device comprising a hemostatic coating comprising oligomerized polyphenol, the device configured so the oligomerized polyphenol comes in contact with a body fluid.

In a related aspect, the disclosure provides a method for promoting clotting at a target location in or on the body comprising placing the medical device with the hemostatic coating comprising oligomerized polyphenol in or on a target location in the body, wherein the coating contacts body fluid and promotes clotting at the target location.

In another aspect, the disclosure provide an article configured for use in an in vitro diagnostic assay or cell culture, the article comprising a coating comprising oligomerized polyphenol. The coating on such articles can be useful for adsorbing molecules for detection assays, or for improving cell culture conditions.

In an associated aspect, the disclosure provides a method for promoting adsorption of a biological macromolecule to a surface of an article in an in vitro diagnostic assay or cell culture. The method includes steps of contacting an article comprising a coating comprising oligomerized polyphenol with a composition comprising a biological macromolecule, wherein the coating promotes adsorption of the biological macromolecule to the oligomerized polyphenol via hydrogen bonding.

BRIEF DESCRIPTION OF THE FIGURES

The disclosure may be more completely understood in connection with the following drawings, in which:

FIG. 5 is a graph showing results of an assay of plasma clotting time on coated and uncoated substrates.

Figure 1A:
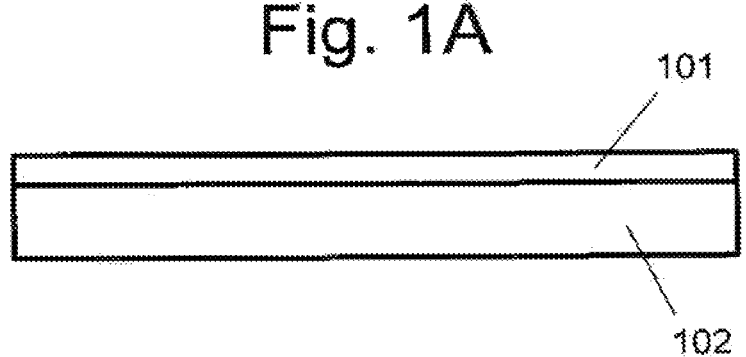
FIG. 1A is a schematic view of cross section of a medical device having a single layer oligomerized polyphenol coating.

While the disclosure is susceptible to various modifications and alternative forms, specifics thereof have been shown by way of example and drawings, and will be described in detail. It should be understood, however, that the disclosure is not limited to the particular embodiments described. On the contrary, the intention is to cover modifications, equivalents, and alternatives falling within the spirit and scope of the disclosure.

DETAILED DESCRIPTION OF THE ILLUSTRATIVE EMBODIMENTS

A "polyphenol" according to the disclosure, refers to an organic molecule having two to up to about 20 phenolic units. Exemplary polyphenols can optionally be characterized by one or more of the following properties a non-polymeric molecule; a molecular weight in the range of about 200-5000 Da; 1-3 hydroxyl groups per phenolic unit, and having 5-8 aromatic rings per 1000 Da. Exemplary polyphenols include two or more phenolic units linked together. Exemplary phenolic units are selected from resorcinol, pyrocatechol, pyrogallol, phloroglucinol, and mixtures thereof. The phenolic unit can linked via various chemical groups, such as ester groups, ether groups, or by C—C groups.

In some cases the polyphenol can be formed by the esterification of one or more phenolic acid(s), such as gallic acid (3,4,5-trihydroxybenzoic acid), around a carbohydrate core, such as glucose. Tannic acid (compound A) is an example of one type of polyphenol that can be formed by such a reaction, and has the following structure:

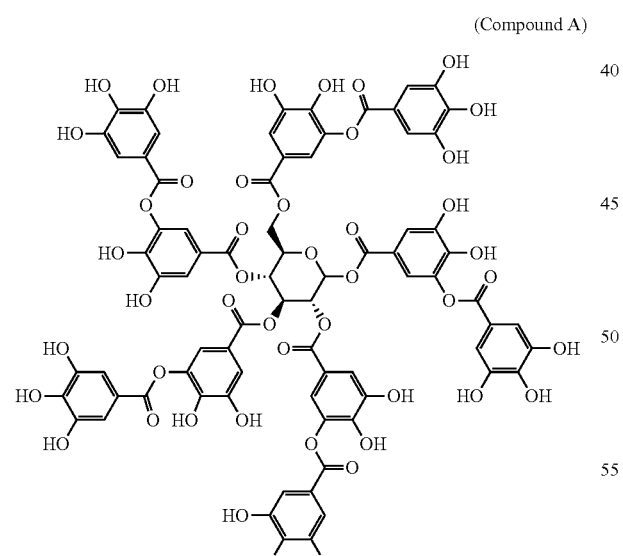

(Compound A)

In some cases the polyphenol is an ester of a phenolic acid(s), such as gallic acid, with another molecule containing phenolic and non-phenolic hydroxyl groups, such as gallecatechol. Epigallocatechin-3-gallate (EGCG; compound B), epicatechin-3-gallate (ECG; compound C); theaflavin-3-gallate (compound D), and ellagitannin (compound B); are examples of polyphenols formed from the esterification of gallic acid with another molecule containing phenolic and non-phenolic hydroxyl groups.

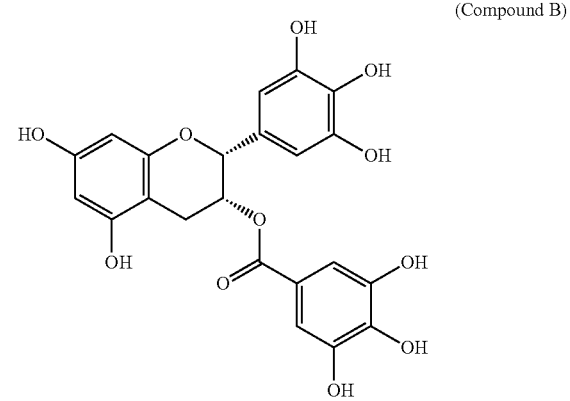

(Compound B)

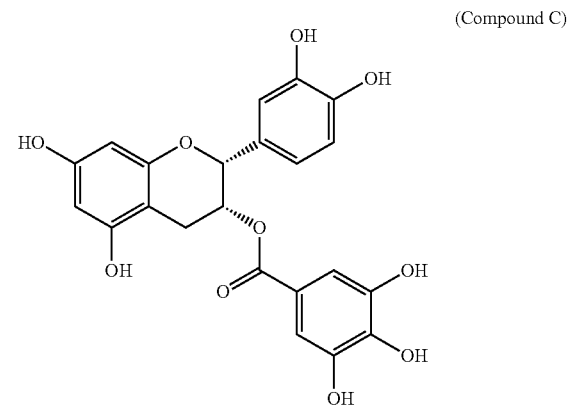

(Compound C)

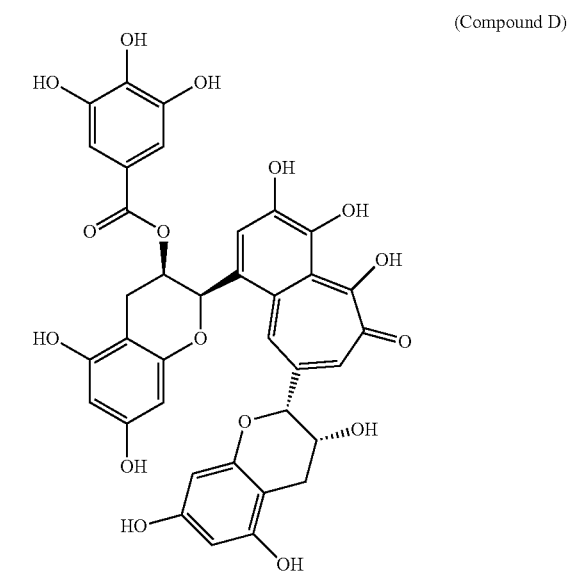

(Compound D)

(Compound E)

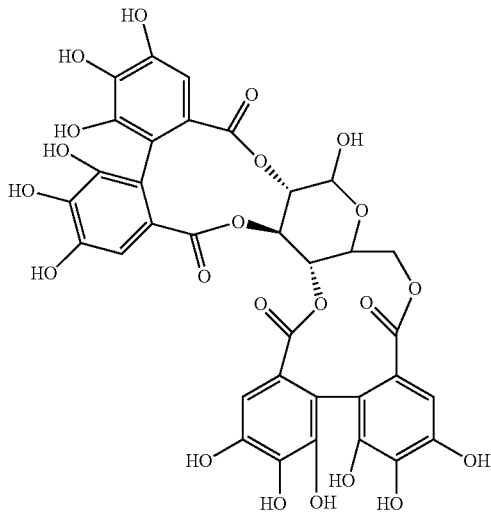

Another exemplary polyphenol is epigallocatechin:

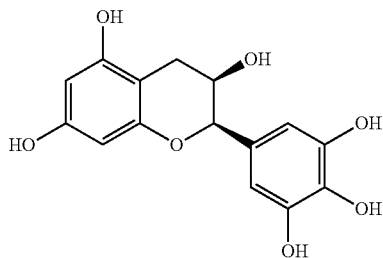 [SMILES: Oc1cc(O)c2c(c1)O[C@H](c1cc(O)c(O)c(O)c1)[C@H](O)C2]

A coating solution can be formed by including a polyphenol in a solvent. A single polyphenol, or a combination of polyphenols, can be dissolved or suspended in a coating solution at a concentration suitable for forming a coating on the surface of an article. Exemplary concentrations of polyphenol are in the range of about 1 ng/mL to about 10 mg/mL, or about 0.5 mg/mL to about 5 mg/mL, such as about 2 mg/mL (e.g., tannic acid at about 2 mg/mL).

Coating of a substrate can be carried out various ways. In mane modes of practice, the polyphenol is dissolved or suspended in a coating solution having a basic pH, such as above 7, such as in the range of about 7.5 to about 9.5, or more specifically in the range of about 8.0 to 8.5. Exemplary basic coating solutions can be made using a solvent such as water and a biocompatible base, such as sodium bicarbonate (e.g., at about 0.5 M). Other biocompatible weak bases in include ammonia, ammonium hydroxide, urea, piperidine, imidazole, potassium carbonate, sodium carbonate, potassium bicarbonate, and pyridine, or combinations thereof. In other modes of practice, the polyphenol can be dissolved or suspended in a coating solution at a pH less than 7. To induce oligomerization of the polyphenol the pH of the solution can subsequently be raised to an alkaline pH. Alternatively, a coating solution including the polyphenol in a solvent can be dip coated onto a device, allowed to dry, and then put in a higher pH buffer to affect crosslinking. The coating solution can also include a neutral salt, such a sodium chloride, at a concentration in the range of about 0.15 M to about 0.75 M, or more specifically at about 0.5 M.

If desired, one or more optional components can be included in the polyphenol coating solution as long as the component(s) does not interfere with the ability of the polyphenol to oligomerize and form a coated layer on the article surface. For example, the polyphenol costing solution may optionally include one or more polymeric components, such as polyamines, or poly(acrylic acid).

The first coating solution can be applied to a substrate. Prior to application of the first coating solution to the substrate, one or more of many different pretreatment steps can be taken. In some embodiments, the surface of the substrate can be cleaned. For example, the surface can be wiped or dipped into an alcohol such as isopropyl alcohol. In some embodiments, the substrate can be put into a detergent solution such as a VALTRON® solution and sonicated. In some embodiments the surface of the substrate can be sterilized.

Many different techniques can be used to apply the solution to the substrate. By way of example, exemplary techniques can include drop coating, blade coating, dip coating, spray coating, and the like. In one mode of coating, the solution is applied by drop coating. In other modes of coating, the substrate can be immersed into the polyphenol coating solution for a period of time sufficient for the coated layer of oligomerized polyphenol to form on the article surface. In exemplary modes of practice the article is immersed in a polyphenol coating solution. The article is maintained in the solution for a period of time greater than 5 seconds, greater than 1 minute, greater than 0 minutes, greater than 30 minutes, such as in the range of about 1 minute to about 2 hours. The article can then be rinsed using a liquid such as water to remove any excess coating material(s).

The oligomerized polyphenol layer can be formed without requiring an oligomerization polymerization initiator, such as a light activated polymerization initiator. Therefore the coating solutions and processes are particularly useful to forming a coated layer on an article surface that where it is difficult to provide light. For example, the coating solutions and processes can be used to form an oligomerized polyphenol layer on a substrate having a complex geometry, or one having an inner surface, such as surfaces of medical devices. These inner surfaces may not be accessible to other forms of energy, such as light, which alternatively may be used to activate and bind coating reagents to surfaces. Examples of substrates that have inner surfaces include, for example, stets, catheters such as PTCA catheters and hemodialysis catheters, hemodialysis membranes, and other devices having inner surfaces. These substrates can be formed, for example, from a complex architecture of materials, or contain many pores.

An "oligomerized" polyphenol layer refers to a water-insoluble coated layer including crosslinked polyphenol molecules. Without intending to be bound by theory, the basic coating solution is believed to promote oligomerization of the polyphenols and formation of an oligomerized polyphenol layer by oxidation of the polyphenol, deprotonation of phenolic hydroxyl groups, rearrangement, and phenol-phenol crosslinking via the phenolic groups. The molecular mechanism of forming the oligomerized polyphenol layer is believed to resemble the formation of a polydopamine coating as described by Lee et al. (Science 318:426-430, 2007).

In another mode of practice, an oligomerized polyphenol layer is formed by including in the coating composition an inorganic molecule that can coordinate with chemical groups of the polyphenol molecules and thereby form crosslinks. For example, a metal ion such as iron (Fe) can coordinate with deprotonated phenolic hydroxyl groups from up to three phenolic groups as taught by Ejima et al. (Science 318:426-430, 2007).

oligomerized polyphenol per se, provides a useful surface modification for medical articles desirably having a hemostatic property. A "hemostatic" property refers to the ability to promote "hemostasis" which is the clotting of blood.

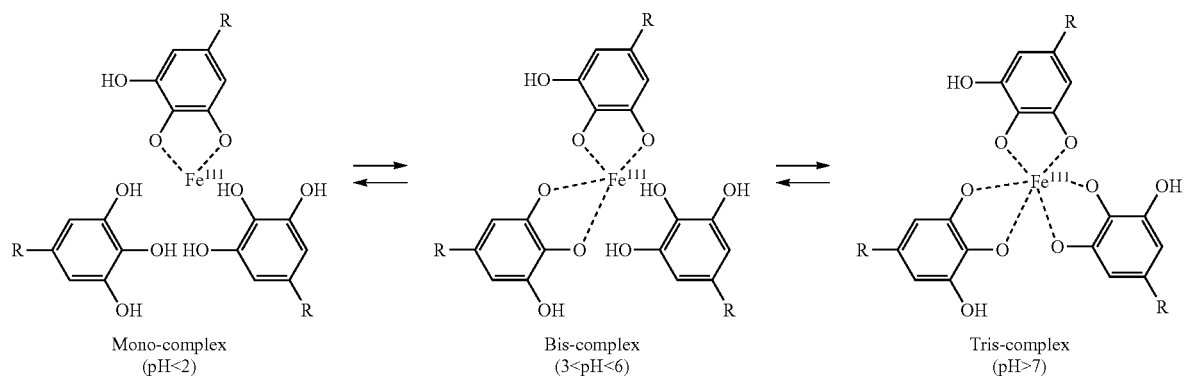

Mono-complex
(pH<2)

Bis-complex
(3<pH<6)

Tris-complex
(pH>7)

Embodiments of the disclosure include coatings that have an oligomerized polyphenol layer that comes in contact with a body fluid, a tissue, a composition used for a detection analysis, or cell culture media. The oligomerized polyphenol can serve to attach or bond one or more components from body fluid (e.g., fibrinogen), or components from a composition used for an in vitro assay (e.g., antibodies or analytes), or components from a cell culture composition.

Figure 1B:
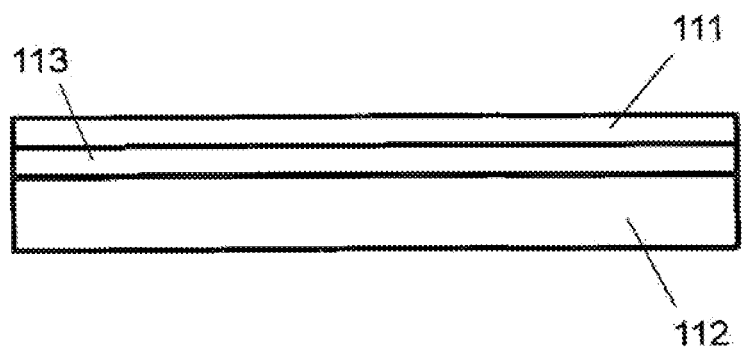
FIG. 1B is a schematic view of cross section of a medical device having a multi-layer coating with oligomerized polyphenol layer.
Figure 3A:
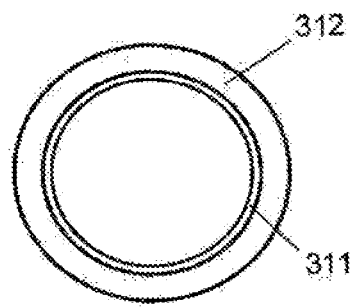
FIG. 3A is a schematic view of cross section of a medical device with a lumen having a single layer oligomerized polyphenol coating on the inner diameter of the device.

As such, the oligomerized polyphenol layer can be sole coated layer in the coating, or can be the "outermost" or "t p" layer if the coating includes more than one layer. Optional additional layer(s) may be between the oligomerized polyphenol layer and the device surface. FIG. 1A is a coating embodiment wherein an oligomerized polyphenol layer 101 is in direct contact with a device surface 102. FIG. 1B is a coating embodiment wherein an oligomerized polyphenol layer 111 is the outermost layer with a tie (or intermediate) layer 113 in contact with a device surface 112. FIG. 3A is a coating embodiment showing a cross section of a medical device with a lumen (such as a catheter), wherein an oligomerized polyphenol layer 311 is present on the inner diameter of a device surface 312. Exemplary substrate materials and materials for optional tie or intermediate layers are known in the art.

The oligomerized polyphenol layer (e.g., 101, 111, or 311) can be very thin, such as less than 100 nm, less than 50 nm, less than 25 nm, less than 10 nm, less than 5 nm (upper limits), or greater than 0.1 nm, greater than 0.25 nm, greater than 0.5 nm, greater than 1 nm, greater than 2 nm (lower limits), or in a range of any combination of these lower and upper limits.

Figure 4:
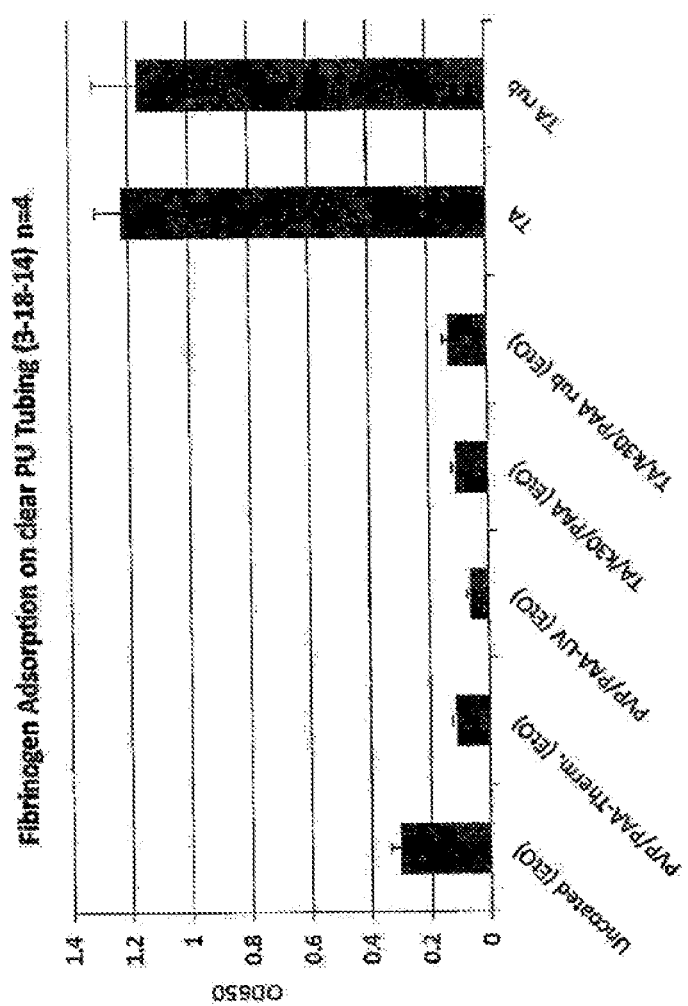
FIG. 4 is a graph showing results of an assay of fibrinogen adsorption on coated and uncoated substrates.

Experimental studies associated with the disclosure have shown the oligomerized polyphenol layer was able to promote significant fibrinogen adsorption (see FIG. 4). Fibrinogen is a protein factors involved in the clotting cascade, and its adherence to a coated surface of a medical device that contacts blood can promote attachment of other coagulation factors. Fibrinogen adhesion can be followed by fibrin and von Willebrand factor (vWF) on the device surface, which may be characterized by a loosely structured matrix. This phase can also be characterized by platelet adhesion.

In addition, the polyphenol layer was able to promote shortened plasma clotting times (see FIG. 5). Therefore, the Various medical articles or devices that are implanted or inserted in the body, or that are placed in contact with a body tissue can be provided with an oligomerized polyphenol hemostatic coating.

In some embodiments, the oligomerized polyphenol hemostatic coating is used in conjunction with an occlusion device for occluding any sort of target area within the body. Occlusion devices include implantable medical devices that are delivered to a target area of the body and that are intended to function to prevent movement of body fluids through or into the area n which the device has been delivered. Thrombosis and the formation of a clot in association with the occlusion device generally aid in establishing the hemostatic function. Occlusion can be established by delivering the device to a target area and allowing the oligomerized polyphenol hemostatic coating to promote formation of fibrin clot, thereby physically occluding the target area. Occlusion articles with an oligomerized polyphenol hemostatic coating can be useful for the selective occlusive of vasculature, including arteries, veins, fistulas, aneurysms, fallopian tubes, bile ducts, and the like. The oligomerized polyphenol hemostatic coating can be used in connection with vascular occlusion coils, wires, or strings that can be inserted into aneurysms.

An oligomerized polyphenol hemostatic coating can also be formed on a porous surface of a medical article. An article having a "porous surface" refers to any article having a surface with pores on which an oligomerized polyphenol hemostatic coating can be formed. In some cases, the pores can be of a physical dimension that permits in-growth of tissue.

In many cases the porous surface of the article is a fabric or has fabric-like qualities. The porous surface can be formed from textiles, which include woven materials, knitted materials, and braided materials. Particularly useful textile materials am woven materials which can be formed using any suitable weave pattern known in the art.

The porous surface can be that of a graft, sheath, cover, patch, sleeve, wrap, casing, and the like. These types of articles can function as the medical article itself or be used in conjunction with another part of a medical article. For example, the oligomerized polyphenol hemostatic coating can be used in conjunction with fabrics, such as cardiac patches, sheaths, and grafts. In these embodiments, a procoagulant coating can be used to generate a hemostatic fibrin clot in association with the coated fabric. These coated articles can be used to prevent the flow of blood within the body in the location the coated article is intended to function.

Fabrics can be prepared from synthetic addition or condensation polymers such as polyesters, polypropylenes, polyethylenes, polyurethanes, and polytetrafluoromethylenes. Polyethylene terephthalate (PET) is a commonly used polymer in fabrics. Blends of these polymers can also be utilized in the preparation of fibers, such as monofilament or multi-filament fibers, for the construction of fabrics. Commonly used fabrics include those such as nylon, velour, and DACRON™.

Surgical patches can be used in various medical procedures to prevent blood flow. A surgical patch having the oligomerized polyphenol hemostatic coating can rapidly generating a fibrin clot associated with the patch, thereby improving hemostatic function.

Other particular contemplated porous surfaces include those of cardiac patches. These can be used to decrease suture line bleeding associated with cardiovascular reconstructions.

The oligomerized polyphenol layer can also be used as a coating on the surface of an in vitro diagnostic article. The coating can be useful for promoting the attachment of a biological molecule, such as a peptide, protein, nucleic acid, or polysaccharide, to the surface. The protein can be an antibody or antibody fragment, or an analyte that is a peptide or protein.

The oligomerized polyphenol layer can be applied to the in vitro diagnostic article over its entire surface, or over a selected portion or portions of the surface. For example, the oligomerized polyphenol layer may be applied in a certain pattern on the device surface to promote adsorption of the biological molecule according to the pattern.

The oligomerized polyphenol layer can be formed on any suitable assay article, such as an assay vessel, or portion thereof. An assay article can be any article on, or in which, analyte detection, such as by ELISA, can be performed. The assay article can be made from material such as glass (e.g., surface modified glass), quartz, silicon, metals, metal oxides or plastic, such as polystyrene, polyolefins, polypropylene, and polycarbonate. Exemplary assay articles are single and multi-well plates, such as medium and smaller-welled plastic plates such as 6, 24, 96, 384, and 1536 well plates. These are commonly known in the art as microtiter plates, microplates, or microwell plates. Exemplary plates for use in in vitro diagnostic assays in each well hold from microliter to milliliter volumes of liquid. Other types of assay vessels that can be used for analysis include capillary tubes. The assay article having an oligomerized polyphenol layer can optionally be included in a kit, or can be supplied by the user to carry out an in vitro diagnostic assay.

The oligomerized polyphenol layer can promote adsorption of a biological macromolecule to the coated surface. For example, in some modes of practice, an article having an oligomerized polyphenol coating is contacted with an antibody-containing composition to promote adsorption of the antibody to the oligomerized polyphenol via hydrogen bonding. Areas of the oligomerized polyphenol coating can then be blocked with a polymer, which can also associate via hydrogen bonding, to block subsequent non-specific analyte or antibody interaction. The oligomerized polyphenol layer can also be used as a coating on the surface of cell culture vessel. The coating can be useful for passivating the surface of the vessel to prevent unwanted adsorption of components of the cell culture vessel wall. A passivating or cell binding component, such as a synthetic or natural polymer, can be hydrogen bonded to the oligomerized polyphenol layer. Alternately, the coating could provide for attachment of components that promote cell attachment. Examples of components that provide promote cell attachment include collagen, fibronectin, laminin, and cell adhesion-promoting peptides such as ROD.

A "cell culture vessel" is an example of a cell culture article and, as used herein, means a receptacle that can be coated with an oligomerized polyphenol coating and can contain media for culturing a cell or tissue. The cell culture vessel may be made from a glass, plastic, or even from metals, such as those metals used to make medical devices. Preferably the plastic is non-cytotoxic. Exemplary cell culture vessels include, but are not limited to, single and multi-well plates, including 6 well and 12 well culture plates, and smaller welled culture plates such as 96, 384, and 1536 well plates, culture jars, culture dishes, petri dishes, culture flasks, culture plates, culture roller battles, culture slides, including chambered and multi-chambered culture slides, culture tubes, coverslips, cups, spinner bottles, perfusion chambers, bioreactors, and fermenters.

Figure 2A:
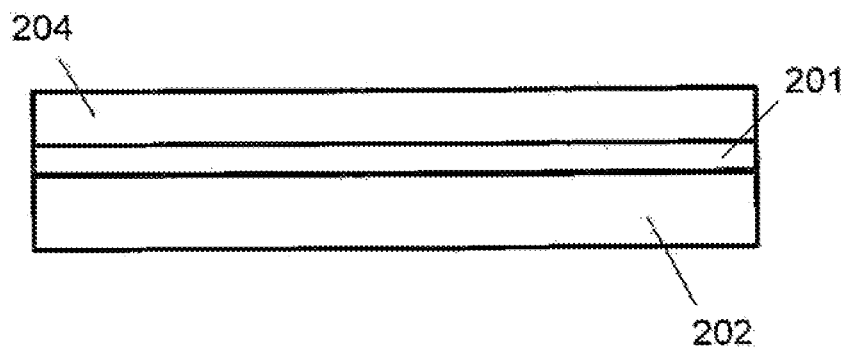
FIG. 2A is a schematic view of cross section of a medical device having a multi-layer coating with oligomerized polyphenol layer.

In providing a coated cell culture vessel, a coating process, such as one described herein, can be used to provide an oligomerized polyphenol coating to a wall of a cell culture vessel. The coating method is advantageous for those vessels having surfaces wherein it is difficult to deliver light otherwise used for initiating a polymerization initiator. After a surface of the cell culture vessel is provided with an oligomerized polyphenol coating it can be contacted with a composition that includes a material that can adsorb to the oligomerized polyphenol coating to passivate the surface and prevent non-specific binding of cell culture components to the vessel. Alternatively, the adsorbed material can promote the binding of cells to the coated surface. Embodiments of the disclosure also include coatings that have an oligomerized polyphenol layer that is an intermediate layer. The oligomerized polyphenol layer can be in direct contact with a device surface, in direct contact with a second coated layer that is distal to the device surface, or both. One or more components of the second coated layer, such as a natural or synthetic polymer(s), can be hydrogen bonded to the oligomerized polyphenol layer FIG. 2A is a coating embodiment wherein an oligomerized polyphenol layer 201 is in direct contact with a device surface 202, and a second coated layer that includes a natural or synthetic polymer 204 is the outermost layer. Hydrogen bonding between the oligomerized polyphenol and the natural or synthetic polymer can be present at the interface between layers 201 and 204. Optionally, a tie layer (not shown) can be present between the oligomerized polyphenol layer 201 and the device surface 202.

Figure 2B:
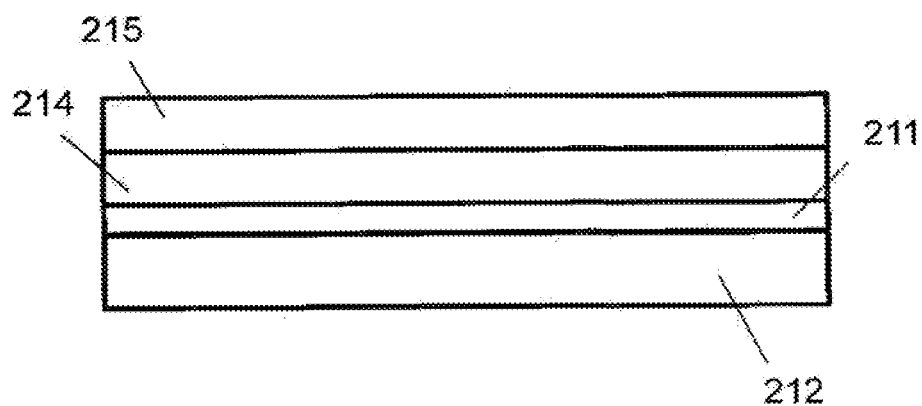
FIG. 2B is a schematic view of cross section of a medical device having a multi-layer coating with oligomerized polyphenol layer.

FIG. 2B is a coating embodiment wherein an oligomerized polyphenol layer 211 is in direct contact with a device surface 212, an intermediate second coated layer 214 that includes a natural or synthetic polymer, and a third coated layer 215 is the outermost layer. Bonding between the natural or synthetic polymer of the second coated layer 214 and a component of the third coated layer 215 may or may not exist. In some arrangements, there is hydrogen bonding between the natural or synthetic polymer of the second coated layer 214 and a component of the third coated layer 215.

Figure 3B:
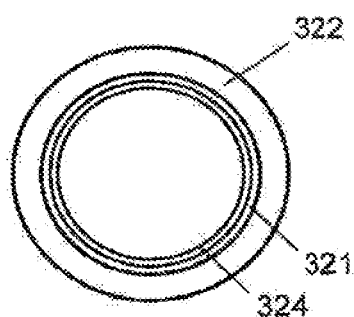
FIG. 3B is a schematic view of cross section of a medical device with a lumen having a multi-layer coating on the inner diameter of the device with an oligomerized polyphenol layer.

FIG. 3B is a coating embodiment showing a cross section of a medical device with a lumen (such as a catheter), wherein an oligomerized polyphenol layer 321 is present on the inner diameter of a device surface 322, the coating further comprising a layer 324 with a natural or synthetic polymer that is hydrogen bonded to the oligomerized polyphenol.

Optionally, the costing can include additional coated layers (e.g., fourth, fifth) that can be present as intermediate or outer coated layers on the device.

The thickness of a coating that includes the oligomerized polyphenol layer (e.g., 201 or 211) and second coated layer (e.g., 204, 214, 324) can vary depending on the coating materials and process used for forming the coating. The coating can have a thickness of less than 2 μm, less than 1 μm, less than 500 nm, less than 250 nm, less than 100 nm (upper limits), or greater than 1 nm, greater than 2.5 nm, greater than 5 nm, greater than 10 nm, greater than 25 nm (lower limits), or in a range of any combination of these lower and upper limits. The costing can optionally be described in terms of the ratio of the thickness of the oligomerized polyphenol layer (e.g., 201, 211, 321) and second coated layer (e.g., 204, 214, 324).

In some embodiments, the second layer includes a polymer capable of bonding to the oligomerized polyphenol of the first coated layer. A test for the ability of a polymer to hydrogen bond to the oligomerized polyphenol may be carried out by staining the coasting with toluidine blue and testing its durability.

Exemplary polymers include natural and synthetic polymers. Natural polymers include polysaccharides, polypeptides, and nucleic adds. Exemplary polysaccarides are methylcellulose and hydroxyethylcellulose. Exemplary synthetic polymers include poly(n-isopropylacrylamide), poly(n-vinylcaprolactam), poly(ethylene oxide), and poly(vinyl alcohol).

The natural or synthetic polymers can be dissolved or suspended in a second coating composition, which can then be applied to the oligomerized polyphenol layer. In exemplary methods, the natural or synthetic polymer is added to a polar solvent, such as water, in an amount in the range of about 0.5 mg/mL to about 50 mg/mL, about 2 mg/mL to about 40 mg/mL, or about 5 mg/mL to about 25 mg/mL. Examplary solvents include water, alcohols (e.g., methanol, ethanol, n-propanol and isopropanol), amides (e.g., dimethylformamide, N-methylpyrrolidone), ethers (e.g., tetrahydrofuran (THF), dipropyl ether and dioxolane), and nitriles (e.g., acetonitrile).

The second coating composition can be applied to the first coated layer of oligomerized polyphenol in any suitable manner under conditions to promote hydrogen bonding of the polymer to the oligomerized polyphenol. Excess unbound polymer can be removed during a washing step.

In some embodiments, the second layer includes a vinyl pyrrolidone polymer. As used herein a "vinyl pyrrolidone polymer" refers to polymers including vinyl pyrrolidone monomeric units. The vinyl pyrrolidone polymer can be a vinyl pyrolidone homopolymer or a vinyl pyrrolidone copolymer including vinyl pyrrolidone and one or more (e.g., two, three, four, five, etc.) other monomeric units that are different than vinyl pyrrolidone. In embodiments, in a poly(vinyl pyrrolidone) copolymer, the vinyl pyrrolidone can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater 85% (mol) or greater, 90% (mol) or greater, 92.5% (mol) or greater, 95% (mol) or greater, 97.5% (mol) or 99% (mol) or greater. In exemplary embodiments, vinyl pyrrolidone is present in the copolymer in the range of about 75% (mol) to about 97.5% (mol), about 85% (mol) to about 97.5% (mol), or about 90% (mol) to about 97.5% (mol).

Other monomers that can be copolymerized with vinyl pyrrolidone to provide the vinyl pyrrolidone polymer include, but are not limited to acrylamide, methacrylamide, acrylic acid, acrylamido-2-methylpropanesulfonate (AMPS), methacrylic acid, methyl acrylate, methyl methacrylate, hydroxyethyl methacrylate, hydroxyethyl acrylate, glyceryl acrylate, glyceryl methacrylate, ethylene glycol, and derivatives of these monomers.

For example, in some embodiments, the second coated layer includes a vinyl pyrrolidone polymer comprising a photoreactive group (e.g., photo-PVP). Reagents and methods for the preparation of photo-PVP can be found in references such as U.S. Pat. Nos. 4,979,959; 5,002,582; 5,263,992; 5,414,075; 5,512,329; and 5,637,460, the teaching of which are incorporated herein by reference. In some modes of practice, photo-PVP can be formed by the copolymerization of 1-vinyl-2-pyrrolidone and N-(3-aminopropyl (meth)acrylamide), which then can be derivatized with an acyl chloride (such as, for example, 4-benzoylbenzoyl chloride) under Schotten-Baumann conditions. That is, the acyl chloride reacts with the amino group of the N-(3-aminopropyl) moiety of the copolymer. An amide is formed resulting in the attachment of the aryl ketone to the polymer.

A vinyl pyrrolidone polymer comprising a photoreactive group can also be prepared by copolymerizing vinyl pyrrolidone with a monomer derivatized with a photoreactive group. Exemplary monomer derivatives include aryl ketone derivatives of hydrophilic free radically polymerizable monomers such as acrylamide, methacrylamide and AMPS. One exemplary methacrylamido-based monomer with a pendent photoreactive groups is N-[3-(4-benzoylbenzamido) propyl]methacrylamide (BBA-APMA), the synthesis which is described in Examples 1-3 of U.S. Pat. No. 5,858,653 (Duran et ad.) Another exemplary methacrylamide-based monomer with a pendent photoreactive group is N-[3-(7-methyl-9-oxothioxanthene-3-carboxamido)propyl] methacrylamide (MTA-APMA), the synthesis which is described in Examples 1-2 of U.S. Pat. No. 6,156,345 (Chudzik et al.)

In some embodiments, a third coated layer that includes an acid group-containing polymer is formed in contact with the second coated layer. An "acid group-containing polymer" refers to polymer that has acid groups presented on the polymer chain. Acidic groups include, for example, sulfonio acids, carboxylic acids, phosphonic acids, and the like. Exemplary salts of such groups include, for example, sulfonate, carboxylate, and phosphate salts. Exemplary counter ions include alkali, alkaline earths metals, ammonium, protonated amines, and the like. If one or more counter ions are used, the acid groups of the acid group-containing polymer are partially neutralized. For example a molar percentage of the acid groups can be neutralized with counter ions, such as in the range of x to y, wherein x toy are selected from about 1%, 5%, 10%, 15%, 20%, 25%, 30%, 40%, 50%, 60%, 70%, 80%, or 90%, wherein x is less than y.

Exemplary carboxylic acid-group containing monomers that can be used to prepare the acid group-containing polymer, include, but are not limited to acrylic acid, methacrylic acid, itaconic acid, monomethyl itaconic acid, maleic anhydride, fumaric acid, and crotonic acid, and salts thereof. Exemplary sulfonic acid-group containing monomers that can be used to prepare the acid group-containing polymer, include, but are not limited to acrylamido-2-methylpropanesulfonic acid (AMPS), 2-(meth)acylamido-2-methylpropane sulfonic acid, vinyl sulfonic acid, 2-sulfoethyl methacrylate, and salts thereof copolymers made from a combination of two or more different acid-group containing monomers can be used, or copolymers made from one or more acid-group containing monomers and one or more non-acid group containing monomers can be used. These copolymers can be random copolymers, block copolymers, graft copolymers or blends thereof.

Other exemplary carboxylic acid-containing monomers that can be used to prepare the acid group-containing copolymers include styrene and maleic anhydride copolymerized to produce styrene-maleic anhydride copolymer (PSMA). Yet other exemplary carboxylic acid-containing monomers are described in "Hydrogen-Bonded Interpolymer Complexes; Formation, Structure and Applications" Chapters 1 and 7, Eds. Vitally V. Khutoryanskiy and Georgios Stalkos (2009).

The acid group-containing polymer may optionally be described with reference to its pH. For example, the acid group-containing polymer may have a pH in the range of about 1 to about 5, about 1.2 to about 5, about 1.5 to about 5, about 2.5 to about 5, about 2.75 to about 4.5, or about 3 to about 4.25.

The third coated layer that is a top coating can comprise an acrylic acid polymer. As used herein an "acrylic acid polymer" refers to polymers including acrylic acid monomeric units. The acrylic acid polymer can be an acrylic acid homopolymer or a acrylic acid copolymer including acrylic acid and one or more (e.g., two, three, four, five, etc.) other monomeric units that are different than acrylic acid. In embodiments, in a poly(acrylic acid) copolymer, the acrylic acid can be the primary monomer (molar quantity), such as present in an amount of greater than 50% (mol), 55% (mol) or greater, 60% (mol) or greater, 65% (mol) or greater, 70% (mol) or greater, 75% (mol) or greater, 80% (mol) or greater, 85% (mol) or greater, 90% (mol) or greater, 92.5% (mol) or greater, 95% (mol) or greater, 97.5% (mol) or 99% (mol) or greater. In exemplary embodiments, acrylic acid is present in the copolymer in the range of about 75% (mol) to about 100% (mol), about 85% (mol) to about 100% (mol), about 95% (mol) to about 100% (mol), or about 98% (mol) to about 100% (mol).

In some embodiments, the acrylic acid polymer in the top coating may have an average molecular weight of 150 kDa or greater. In yet other embodiments the acrylic acid polymer in the top coating may have an average molecular weight of 250 kDa or greater, 350 kDa, 450 kDa, 550 kDa, 650 kDa or greater or even in some cases an average molecular weight of 750 kDa or greater.

The acrylic acid polymer of the third coated layer can undergo hydrogen bonding with the natural or synthetic polymer, such as a vinyl pyrrolidone polymer, of the second coated layer. More specifically, hydrogen bonding between the polymers can involve the carbonyl oxygens of both the pyrrolidone ring and the carboxylic acid.

In other embodiments, the third coated layer that is a top costing also includes a cross-linking agent comprising at least two photoreactive groups, or an acrylamide polymer comprising at least one photoreactive group. In some embodiments, the acrylamide polymer can comprise acrylamide, acrylamido-2-methylpropanesulfonate groups (AMPS), and poly(ethyleneglycol) groups. For example, in a specific embodiment, the acrylamide polymer can be N-acetylated poly[acrylamide-co-sodium-2-acrylamido-2-methylpropanesulfonate-co N-(3-(4-benzoylbenzamido) propyl) methacrylamide]-co-methoxy poly(ethylene glycol) monoethacrylate. Reagents and method for the preparation of polymers comprising polyacrylamide in accordance with embodiments herein can be found in can be found in references such as U.S. Pat. Nos. 4,979,959; 5,002,582; 5,263,992; 5,414,075; 5,512,329; and 5,637,460, the teaching of which are incorporated herein by reference.

In embodiments, the second or third coated layer, or both, can include a crosslinking reagent comprising photoreactive groups. The photoreactive group can be an aryl ketone, such as acetophenone, benzophenone, anthrone, and anthrone-like heterocycles (i.e., heterocyclic analogs of anthrone such as those having N, O, or S in the 10-position), or their substituted (e.g., ring substituted) derivatives.

Exemplary cross-linking agents are described in U.S. Publ. Pat. App. No. 2011/0245367, the content of which is herein incorporated by reference in its entirety. In some embodiments, at least one of the first and/or second cross-linking agents may comprise a linking agent having formula Photo$^1$-LG-Photo$^2$, wherein Photo$^1$ and Photo$^2$, independently represent at least one photoreactive group and LG represents a linking group comprising at least one silicon or at least one phosphorus atom, there is a covalent linkage between at least one photoreactive group and the linking group, wherein the covalent linkage between at least one photoreactive group and the linking group is interrupted by at least one heteroatom.

In other embodiments, an ionic photoactivatable cross-linking agent can be used. The ionic photoactivatable cross-linking agent can be a compound of formula 1: $X^1$-Y-$X^2$ where Y is a radical containing at least one acidic group, basic group, or a salt of an acidic group or basic group. $X^1$ and $X^2$ are each independently a radical containing a latent photoreactive group.

For example, a compound of formula 1 can have a radical Y that contains a sulfonic acid or sulfonate group; $X^1$ and $X^2$ can contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy) benzene-1,4-disulfonic acid or salt; 2,5-bis(4-benzoylphenylmethyleneoxy)benzene-1-sulfonic acid or salt; N,N-bis[2-(4-benzoylbenzyloxy)ethyl]-2-aminoethane-sulfonic acid or salt, and the like. See U.S. Pat. No. 6,278,018

In other embodiments of formula 1, Y can be a radical that contains a basic group or a salt thereof. Such Y radicals can include, for example, an ammonium, a phosphonium, or a sulfonium group; suitable counter ions include, for example, carboxylates, halides, sulfate, and phosphate. Exemplary photoactivatable cross-linking agents include ethylenebis(4-benzoylbenzyl-dimethylammonium) salt; hexamethylenebis (4-benzoylbenzyl-dimethylammonium) salt; 1,4-bis(4-benzoylbenzyl)-1,4-dimethylpiperazinediium) salt, bis(4-benzoylbenzyl)hexamethylenetetraminediium salt, bis [2-(4-benzoylbenzyl-dimethylammonio)ethyl]-4-benzoyl-benzylmethylammonium sat; 4,4-bis (4-benzoylbenzyl)morpholinium salt; ethylenebis [(2-(4-benzoylbenzyldimethyl-ammonio)ethyl)-4-benzoyl-benzylmethylammonium] salt; and 1,1,4,4-tetrakis(4-benzoylbenzyl)piperzinediium salt. See U.S. Pat. No. 5,714,360.

Substrates on which the coating can be formed can be partially or entirely fabricated from a metal, ceramic, glass, or the like, or a combination thereof. Substrates can include polymers such as polyurethanes and polyurethane copolymers, polyethylene, polyolefins, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, polyether-polyamide copolymers, and the like. The substrate can be made of a single material, or a combination of materials.

Substrate polymers can also include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacylate, hydroxyethyl acrylate, acrylic acid, methacylic acid, glyceryl acrylate, glyceryl methacrylate, methacrylamide, and acrylamide; vinyls such as ethylene, propylene, vinyl chloride, vinyl acetate, vinyl pyrrolidone, vinylidene difluoride, and styrene. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

In some embodiments, the substrate includes a polymer selected from the group consisting of polyamide, polyimide, polyether block amide (PEBAX), polyether ether ketone (PEEK), high density polyethylene (HDPE), polyethylene, polyurethane, and polyethylene vinyl acetate.

Metals that can be used as substrates in medical articles include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septal defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stem graft catheters; anastomosis devices and anastomotic closures; aneurysm exclusion devices; biosensors including glucose sensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products, vena cave filters, and embolic protection filters and devices and electrophysiology mapping and ablation catheters.

The coating having the first oligomerized polyphenol, the second layer including the synthetic or natural polymer hydrogen bonded to the oligomerized polyphenol, and optionally the third layer acid polymer can have a hemocompatible (blood compatible) property. For example, a medical article with a hemocompatible costing can reduce effects that may associated with placing a foreign object in contact with blood components, such as the formation of thrombus or emboli (blood clots that release and travel downstream). The hemocompatible property of the coating can be observed as compared to a medical device that does not have the coating. Optionally, the coating can be further modified with hemocompatible proteins or peptides to enhance the hemocompatible (blood compatible) property.

An assay for measuring hemocompatibility of a coated surface can be performed using any one of a variety of tests. Techniques, such as including clot-based tests, such an artificial circulation (Chandler loop) using whole blood augmented with platelets (e.g., see Robbie, L. A., et al. (1997) Thromb Hemost. 77:510-5), or the in vitro bovine blood loop, chromogenic or color assays, direct chemical measurements, and ELISAS, are used for coagulation testing (e.g., see. Bates, S. M., and Weitz, J J. (2005) *Circulation*, 112:53-60; and Walenga, J. M., et al. (2004) *Semin Thromb Hemost.* 30:683-695). Whereas clotting assays provide a global assessment of coagulation function, chromogenic tests are designed to measure the level or function of specific factors.

In some embodiments, the coating includes with first (polyphenol) and second layers, with the second layer comprising a polymer that is hydrogen bonded to the first layer, and that also provides a lubricious or low friction surface. The lubricious or low friction surface can facilitate movement of the coated device in relation to a tissue, or can facilitate movement of the coated device in contact with another component of the medical device, or movement of two medical devices in contact with each other. For example, one approach to reducing the friction between a medical device and the environment surrounding the medical device is to apply a lubricious or low friction coating onto the medical device.

The present disclosure may be better understood with reference to the following examples. These examples are intended to be representative of specific embodiments of the disclosure, and are not intended as limiting the scope of the disclosure.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" Is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which the disclosure pertains. All publications and patent applications are herein incorporated by reference to the same extent as if each individual publication or patent application was specifically and individually indicated by reference. Nothing herein is to be construed as an admission that the inventors are not entitled to antedate any publication and/or patent, including any publication and/or patent cited herein.

The disclosure has been described with reference to various specific and preferred embodiments and techniques. However, it should be understood that many variation and modifications may be made while remaining within the spirit and scope of the disclosure.

Example 1: Preparing a Low-Protein Binding Polyphenol Coating

First, a tannic acid tie layer was applied to 7 cm segments of polyurethane (PU) 7F catheters (Solomon Scientific). To prepare a 2 mg/ml tannic acid (TA) solution, 80 mg of TA was dissolved in 40 ml of an aqueous buffer solution containing 0.5 M NaHCO3 and 0.5 M NaCl (final pH of 8.3). Catheter segments were added to the tannic acid solution and gently inverted to remove any trapped air bubbles from the catheter lumens. The catheters were then incubated at 50° C. for one hour without agitation. After the incubation, catheter segments were removed from tannic acid, rinsed thoroughly with water, both internal and outer diameters, and air dried.

Next, for the second layer of the coating, polyvinylpyrrolidone (PVP) was hydrogen bonded to the TA tie layer. TA modified catheters were placed into a PVP solution (K30, BASF, 10 mg/ml in 10 mM phosphoric acid, pH 2.0) for five minutes at room temperature, rinsed with water, and air dried.

Lastly, for the third layer, poly(acrylic acid) (PAA) was hydrogen bonded to the PVP layer. Catheter segments were incubated in a PAA solution (in-house synthesized PAA, 20 mg/ml in water) for five minutes at room temperature. Catheters were then rinsed with water and allowed to air dry at room temperature.

To confirm the presence of the coating, samples of catheter were stained with a positively charged dye, toluidine blue, by submerging the sample in 0.1% w/v toluidine blue water solution for five minutes and then thoroughly rinsing the sample with water to remove excess stain. The sample stained a dark purple indicating the presence of the negatively charged PAA top coat. An uncoated control stained a very faint blue whereas a TA-only control stained a darker blue. A coating without the PAA top coat stained similar to the TA-only control.

Example 2: Fibrinogen Adsorption to Polyphenol Coatings from Human Plasma

To characterize the protein adsorption properties of the coatings, fibrinogen adsorption to coated and uncoated catheters was quantified using an ELISA technique. Polyurethane catheters were cut into 1 cm long samples and placed in 12×75 mm glass test tubes (4 samples/test tube). Human platelet-poor plasma (PPP from George King Bio-Medical) was diluted 1:4 with phosphate-buffered saline (PBS). Two milliliters of diluted PPP was added to each test tube. Samples were incubated for two hours with agitation on an orbital shaker at room temperature. The plasma was aspirated off of the samples and the samples were washed three times with a PBS wash solution containing 0.05% (v/v) Tween 20, pH 7.4. Next, two milliliters of polyclonal anti-human-fibrinogn-HRP (Rockland, Inc., product #200-103-240) was added to each test tube at a dilution of 1:10,000 in PBS. Samples were incubated for 30 minutes with agitation on an orbital shaker at room temperature. The antibody solution was aspirated off and the samples were washed three times with PBS plus Tween-20 wash solution.

Samples were transferred to clean 12×75 mm glass test tubes (1 sample/test tube) and 1 ml of tetramethylbenzidine (TMB) substrate solution was added to each test tube. The samples were incubated for 15 minutes with agitation on an orbital shaker at room temperature. The supernatant was then transferred to a 96-well microtiter plate and the absorbances at 650 nm were read on a spectrophotometer (Molecular Devices, Thermomax microplate reader) with a negative control solution, containing only the chromogen, used as the blank. The absorbances are directly proportional to the surface concentration of HRP and, therefore, also proportional to the concentration of fibrinogen bound to the surface of the materials.

To measure the durability of the coatings, a few coated catheters were included that were subjected to a nitrile gloved finger test. The test consisted of rubbing the sample five times in one direction using light to moderate pressure while the samples were under a stream of water. The sample was rotated about a quarter turn after each rub so that the entire circumference was rubbed at least once.

As shown in the graph of FIG. 4 the PAA coating reduced fibrinogen adsorption compared to uncoated PU catheter, whereas the TA coating substantially increased fibrinogen adsorption. In both cases, rubbing the coating did not have any significant effect.

Example 3: Human Plasma Clotting Times of Polyphenol Coatings

A useful test in determining the hemocompatibility of a surface modification is the partial thromboplastin time (PTT) test. The PTT is a test of the intrinsic (factors VIII, IX, XI, and XII) and common (fibrinogen, prothrombin, factors V and X) pathways of coagulation.

Polyurethane catheters were cut into 0.7 cm long samples and each sample was placed into a 12×75 mm polystyrene test tube. Next, a mixture of plasma and cephalin (a phospholipid platelet substitute) was dispensed to each test tube. Samples were then incubated at 37° C. for 20 minutes. Transferred 200 μl of plasma from each test tube to a 96-well microtiter plate and added 100 μl of warm CaCl2 to each well. Immediately began reading OD at 340 nm every 20 seconds. The time at half maximum absorbance was reported as the clotting time.

As shown in the graph of FIG. 5, a glass control was used as a procoagulant surface and it clotted in less than five minutes. The TA coating clotted twice as fast as the uncoated PU control. Adding the hydrogen bonded PVP K30 and PAA layers significantly slowed the clotting times.

Example 4: Coatings for Immunoassay on 96-Well Microtiter Plates

Nunc maxisorb (polystyrene treated for optimum protein adsorption) and Greiner UV-Star (cyclic polyolefin) 96-well microtiter plates were coated with tannic acid and then evaluated in a model immunoassay.

Figure 6A:
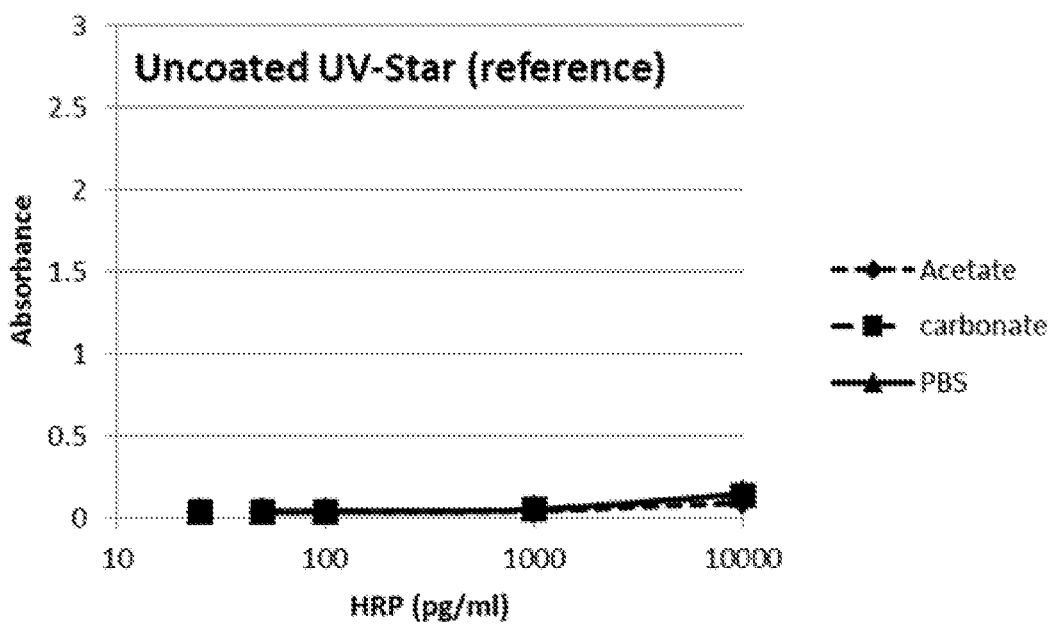
FIGS. 6A-D are graphs showing results of immunoassays on surfaces with and without tannic acid coatings.
Figure 6B:
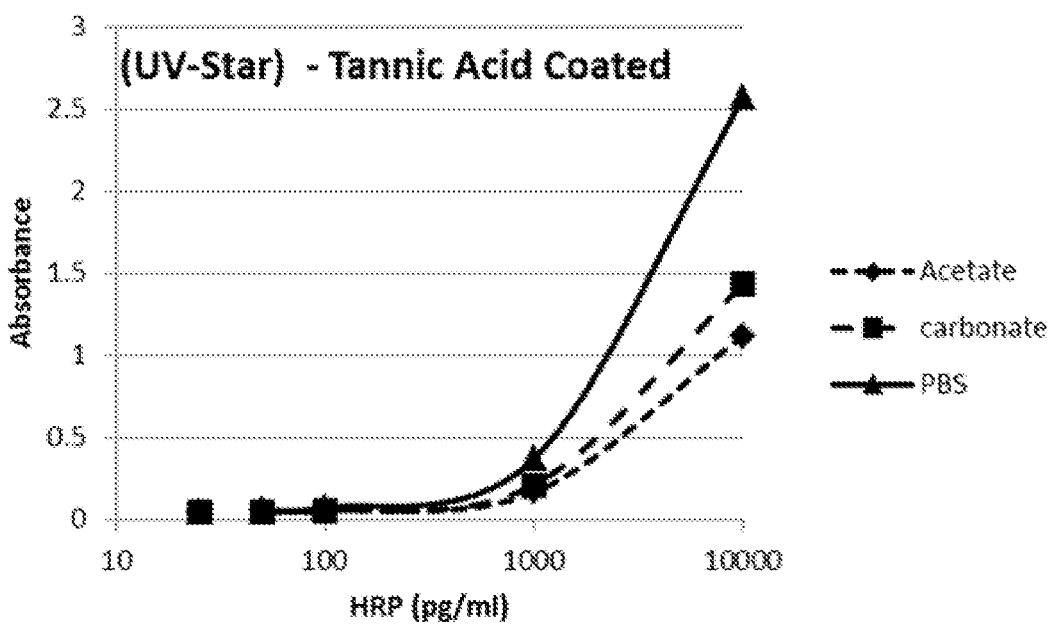
Figure 6C:
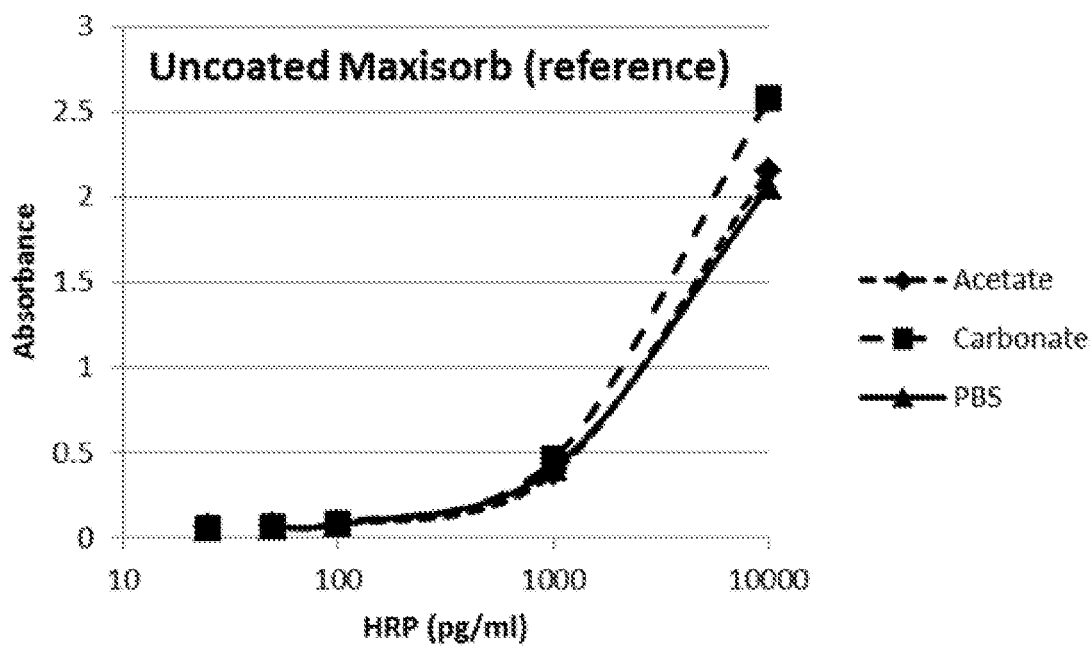
Figure 6D:
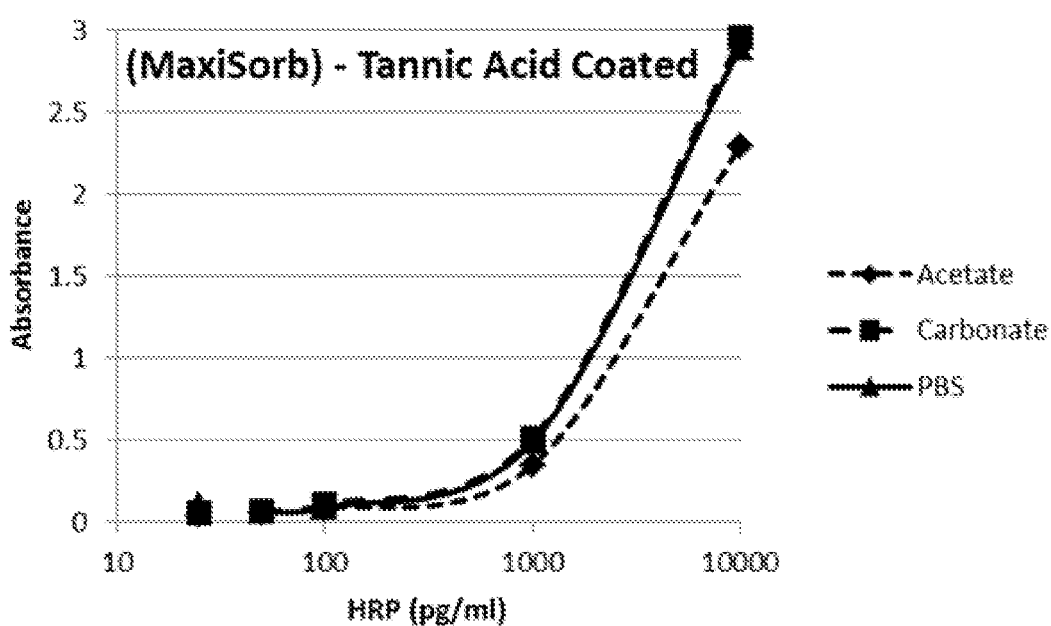

Tannic acid was added to pro-warmed (55° C.) 0.5 M sodium carbonate (pH 8.3) containing 0.5 M NaCl at a tannic acid concentration of 2 g/L. One hundred microliters of this solution was added to each well of the plate, the plate was incubated at 55 C for 5 minutes. The wells were emptied and than washed 4 times with DI water. The plate was allowed to dry. Plates were coated by putting 100 μl/well of rabbit anti horseradish peroxidase (HRP) antibody (Accurate Chemical and Scientific) at 0.86 μg/ml in either of three buffers. The three buffers were 0.05 M sodium carbonate (pH 9.5), phosphate buffered saline (pH 7.2), and 50 mM sodium acetate (pH 5.4). Plates were incubated overnight at room temperature, washed 3× with PBS-Tween20, and 100 μl of StabilCoat (SurModics, Inc.) was added to each well. After a 2 hour incubation plates were aspirated and dried at low humidity. The plates were then used in a model assay that uses horseradish peroxidase (HRP) as the analyte. Plates were washed three times with PBS-Tween20. HRP (100 μl) was added at 25, 50, 100, 1000, or 10,000 pg/ml in PBS-Tween20 to wells. The plate was incubated for 2 hours and then washed 6× with PBS-Tween20. TMB microwell substrate (SurModics, Inc.) was added to the wells (100 μl) and the plate incubated for 20 minutes. Nova-Stop reagent (SurModics, Inc.) (100 μl) was added to the wells and the plate was read at 450 nm. FIGS. 6B and D show that the tannic acid coating vastly improved the assay results on the UV-Star plate and slightly improved the assay results on a plate (MaxiSorb) already optimized for ELISA assays.

What is claimed is:

1. A medical device comprising a water-insoluble hemostatic coating comprising an immobilized oligomerized polyphenol, the device configured so the immobilized oligomerized polyphenol comes in contact with a body fluid, and wherein the hemostatic coating has a thickness of less than 100 nm.

2. The medical device of claim 1 selected from the group consisting of vascular implants and grafts, wound dressings and wound management device, hemostatic barriers, occlusion articles, mesh and hernia plugs, patches, and uterine bleeding patches.

3. A method for promoting clotting at a target location in or on the body comprising placing the medical device of claim 1 in or on a target location in the body, wherein the coating contacts body fluid and promotes clotting at the target location.

4. The method of claim 3 wherein the coating promotes fibrinogen absorption.

5. A medical device comprising an inner surface comprising a water-insoluble coating, the coating comprising an immobilized oligomerized polyphenol, wherein the oligomerized polyphenol is in an oligomerized polyphenol layer having a thickness of less than 100 nm.

6. The medical device of claim 5 wherein the coating is formed on the inner diameter of a catheter.

7. A method for reducing or preventing the adherence of bacteria on a medical device surface, comprising implanting the device of claim 5 in a patient.

8. The medical device of claim 1 wherein the oligomerized polyphenol comprises (a) a polyphenol having a molecular weight in the range of 500-4000 Da, (b) a polyphenol having 12 or more phenolic hydroxyl groups, or both (a) and (b).

9. The medical device of claim 1 wherein (a) the oligomerized polyphenol comprises a polyphenol derived from esterification of a composition comprising gallic acid, (b) the oligomerized polyphenol comprises tannic acid, or both (a) and (b).

10. The medical device of claim 1 wherein the oligomerized polyphenol comprises an inorganic metal ion that crosslinks polyphenols.

11. The medical device of claim 1 wherein the hemostatic coating has thickness of less than 25 nm.

12. The medical device of claim 1 wherein the oligomerized polyphenol is formed by causing oligomerization of the polyphenol using a base.

13. The medical device of claim 5 wherein the oligomerized polyphenol layer has thickness of less than 25 nm.

14. The medical device of claim 5 wherein the oligomerized polyphenol is formed by causing oligomerization of the polyphenol using a base or an inorganic coordinating molecule.

15. The medical device of claim 5 wherein the coating comprises a first layer that is an oligomerized polyphenol layer and a second layer comprising a natural or synthetic polymer that is hydrogen bonded to the oligomerized polyphenol in the oligomerized polyphenol layer.

16. The medical device of claim 15 wherein the first and second coated layers have a combined thickness of less than 250 nm, or less than 100 nm.

17. The medical device of claim 1 wherein the water-insoluble hemostatic coating is formed by applying a coating composition comprising a polyphenol on a medical device surface and causing oligomerization of the polyphenol using a base or an inorganic coordinating molecule.

* * * * *